United States Patent
Patkar et al.

(10) Patent No.: US 10,815,265 B2
(45) Date of Patent: Oct. 27, 2020

(54) PROCESS FOR PREPARATION OF REGADENOSON AND POLYMORPHS THEREOF

(71) Applicant: USV Private Limited, Mumbai (IN)

(72) Inventors: Laxmikant Narhari Patkar, Mumbai (IN); Kamlesh Digambar Sawant, Mumbai (IN); Harish Kashinath Mondkar, Mumbai (IN); Tushar Anil Naik, Mumbai (IN)

(73) Assignee: USV Private Limited, Mumbai (IN)

(*) Notice: Subject to any disclaimer, the term of this patent is extended or adjusted under 35 U.S.C. 154(b) by 0 days.

(21) Appl. No.: 16/455,616

(22) Filed: Jun. 27, 2019

(65) Prior Publication Data

US 2020/0002369 A1    Jan. 2, 2020

(30) Foreign Application Priority Data

Jun. 29, 2018   (IN) .............................. 201821024307

(51) Int. Cl.
*C07H 19/16*   (2006.01)

(52) U.S. Cl.
CPC .......... *C07H 19/16* (2013.01); *C07B 2200/13* (2013.01)

(58) Field of Classification Search
None
See application file for complete search history.

(56) References Cited

U.S. PATENT DOCUMENTS

2016/0024137 A1*  1/2016  Grisenti ............... C07H 19/167
                                                              536/27.4
2018/0127452 A1   5/2018  Kovi et al.

FOREIGN PATENT DOCUMENTS

| IN | 2012MU3310 | * | 8/2014 | ........... C07H 19/167 |
| WO | WO-0078779 A2 | | 12/2000 | |
| WO | WO-2007092372 A1 | | 8/2007 | |

OTHER PUBLICATIONS

Highlights of Prescribing Information for LEXISCAN, Reference ID 3430682, Oct. 2013. (Year: 2013).*

* cited by examiner

*Primary Examiner* — Layla D Berry
(74) *Attorney, Agent, or Firm* — Schwegman Lundberg & Woessner, P.A.

(57) ABSTRACT

The present invention relates to a process for preparation of Regadenoson and polymorphs thereof. In particular, the present invention relates to a process for preparation of Regadenoson Form C.

7 Claims, 7 Drawing Sheets

PROCESS FOR PREPARATION OF REGADENOSON AND POLYMORPHS THEREOF

CLAIM OF PRIORITY

This application claims the benefit of priority under 35 U.S.C. § 119 to Indian Patent Application No. 201821024307, filed on Jun. 29, 2018, which is incorporated by reference herein in its entirety.

FIELD OF THE INVENTION

The present invention relates to a process for preparation of Regadenoson and polymorphs thereof. In particular, the present invention relates to a process for preparation of Regadenoson Form C.

BACKGROUND OF INVENTION

Regadenoson, chemically known as (1-(9-[(4S,2R,3R,5R)-3,4-dihydroxy-5-(hydroxy methyl)oxolan-2-yl]-6-aminopurin-2-yl pyrazol-4-yl)-N-methylcarboxamide and represented by formula (I), is a selective $A_{2A}$-adenosine receptor agonist.

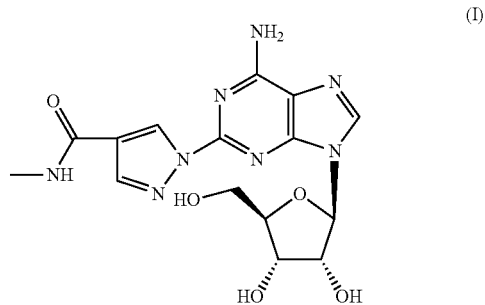 [SMILES: CNC(=O)c1cnn(-c2nc(N)c3ncn([C@@H]4O[C@H](CO)[C@@H](O)[C@H]4O)c3n2)c1]

(I)

Regadenoson is a pharmacologic stress agent indicated for radionuclide myocardial perfusion imaging in patients unable to undergo adequate exercise stress. It is a low affinity agonist for the $A_{2A}$-adenosine receptor, with at least 10-fold lower affinity for the $A_1$ adenosine receptor and weak, if any, affinity for the $A_{2B}$ and $A_3$ adenosine receptors. Activation of the $A_{2A}$-adenosine receptor by Regadenoson produces coronary vasodilation and increases coronary blood flow.

Regadenoson is commercially marketed by Astellas Pharma under the brand name of Lexiscan® in the United States and by Rapidscan Pharma/GE Healthcare under the brand name of Rapiscan® in various European countries. The marketed formulation is a sterile, clear, colorless, non-pyrogenic solution for intravenous administration. It is available as a single-use vial and single-use pre-filled syringe containing Regadenoson 0.4 mg/5 ml (0.08 mg/ml). The recommended dose is 5 ml (0.4 mg regadenoson) administered as a rapid injection into a peripheral vein using a 22 gauge or larger catheter or needle followed by immediate flushing with 5 ml of saline and administering the radionuclide myocardial perfusion imaging agent 10-20 seconds after the saline flush. The radionuclide may be injected directly into the same catheter as Lexiscan®.

WO0078779 describes the process for preparation of Regadenoson. The process disclosed in Example 5 of this patent application involves the reaction of Ethyl 1-{9-[(4S,2R,3R,5R)-3,4-dihydroxy-5-(hydroxymethyl) oxolan-2-yl]-6-aminopurin-2-yl}pyrazole-4-carboxylate with 40% solution of methyl amine in water, at 65° C. for 24 hours. After concentration in vacuo, the residue is purified using prep. TLC. However, the yield, purity and melting point of the product are not provided.

WO2007092372 discloses that Regadenoson is capable of existing in at least three different crystalline forms, referred to as Form A, Form B, Form C and an amorphous product.

Form A has been shown to be a monohydrate and is reported to be the most stable form at ambient temperatures. It is reported to be stable under relative humidity stress conditions upto its melting point. Form B is reported as containing varying amounts of water. It is further reported that it is difficult to reliably reproduce the preparation of this polymorph. The X-ray analysis of the crystals of Form B is reported to be distinctly different from any other polymorph, but it is reported that it is difficult to determine its constitution, as the X-ray analysis gave disordered broad peaks. This document further discloses that Form C could be produced by slurrying 1-{9-[(4S,2R,3R,5R)-3,4-dihydroxy-5-(hydroxy methyl) oxolan-2-yl]-6-aminopurin-2-yl}pyrazol-4-yl)-N-methylcarboxamide in acetonitrile for a long period of time at 60° C. Form C has been shown to be a variable hydrate, which at elevated temperature desolvates to an unstable form. This document also discloses that amorphous Regadenoson is unstable in the presence of atmospheric moisture forming variable hydrates. Use of acetonitrile, which is a class II solvent, is not advisable due to the need to limit its content in the final product to around 410 ppm. To meet this requirement, the product may have to be subjected to harsh conditions, which can in turn affect the quality of the product.

3310/MUM/2012 describes the process for preparation of Regadenoson. It further discloses the process for preparation of Regadenoson Form A and Form C. This document teaches that Regadenoson Form C can be prepared by suspending Regadenoson in acetonitrile or methanol followed by stirring the reaction mixture at 60-65° C. for 5-6 hours to obtain a slurry, which is then filtered to obtain the desired compound. This document teaches the use of class II solvents, which is not recommended, particularly for pharmaceutical substances.

US20180127452 discloses a process for preparation of stable Regadenoson polymorphic form C. The process involves obtaining a solution of Regadenoson in benzyl alcohol solvent, maintaining the reaction mixture to about 10° C. to about 90° C. and isolating stable Form C of Regadenoson. However, use of benzyl alcohol is not feasible, particularly on a large scale due to toxicity issues. Further reducing the residual solvent content in the final product would be a challenge due to the high boiling point of benzyl alcohol.

There exists a need to develop an alternative, simple, cost-effective, reproducible, commercially viable and industrially feasible process for preparation of Regadenoson Form C. The present invention provides a simple, cost-effective, reproducible, commercially viable and industrially feasible process for preparation of Regadenoson Form C.

OBJECT OF THE INVENTION

An object of the present invention is to provide a simple, cost-effective, reproducible, commercially viable and industrially feasible process for preparation of Regadenoson Form C.

Another object of the present invention is to provide substantially pure Regadenoson Form C.

Yet another object of the present invention provides a pharmaceutical composition comprising Regadenoson Form C.

SUMMARY OF THE INVENTION

According to one aspect of present invention, there is provided a process for preparation of Regadenoson Form C comprising the steps of,
a) treating Regadenoson with a $C_1$-$C_3$ alcohol at an elevated temperature to obtain a mixture;
b) maintaining said mixture at the same temperature for at least about 3 hours; and
c) isolating Regadenoson Form C from said mixture.

Preferably, the elevated temperature is a temperature above 70° C.

Preferably, the $C_1$-$C_3$ alcohol is selected from isopropanol, n-propanol or ethanol. Preferably, the mixture is maintained at an elevated temperature for at least about 7 hours.

Preferably, the isolation of Regadenoson Form C is carried out by cooling said mixture to about 70° C.

Preferably, Regadenoson used in the process of the present invention is Regadenoson monohydrate.

Preferably, Regadenoson Form C obtained by the process of the present invention has a moisture content in the range of 0.5-4.4% w/w.

Preferably, Regadenoson Form C is characterized by a X-ray diffraction pattern having peaks at 2-theta values of about 6.16, 10.36, 10.72, 12.32 and 25.41 degrees. Another aspect of the present invention provides a process wherein Regadenoson Form C is further treated with excipient(s) selected from the group consisting of disodium edetate, dibasic sodium phosphate dihydrate, dibasic sodium phosphate anhydrous, monobasic sodium phosphate monohydrate and propylene glycol to obtain a pharmaceutical composition.

DETAILED DESCRIPTION OF THE INVENTION

Figure 1A:
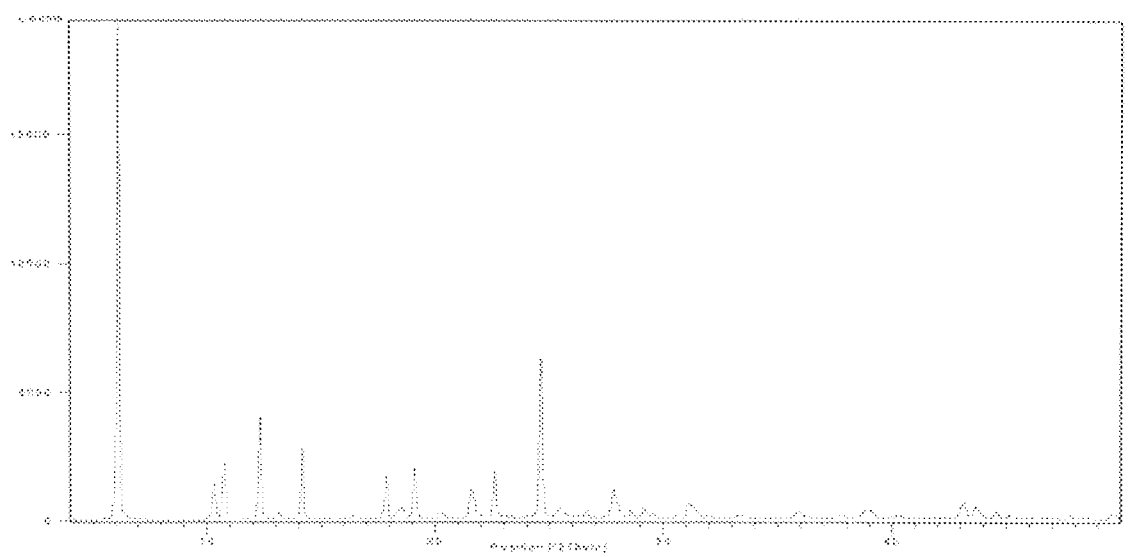
FIG. 1A: XRPD of Regadenoson Form C obtained by the process of the present invention.

The present invention relates to a process for preparation of Regadenoson and polymorphic form thereof. In particular, the present invention relates to a simple, cost effective, reproducible, commercially viable and industrially feasible process for the preparation of Regadenoson Form C.

According to one embodiment of the present invention, there is provided a process for preparation of Regadenoson Form C, comprising the steps of:

a) treating Regadenoson with a $C_1$-$C_3$ alcohol to obtain a mixture; and
b) isolating Regadenoson Form C from said mixture.

Preferably, the mixture obtained in step a) is heated to an elevated temperature.

Preferably, the $C_1$-$C_3$ alcohol is selected from isopropanol, n-propanol or ethanol.

Any known polymorphic form of Regadenoson other than Regadenoson Form C can be used for the preparation of Regadenoson Form C.

Preferably, Regadenoson monohydrate (Form A) is used for the preparation of Regadenoson Form C. The characterization data for Regadenoson monohydrate (Form A) are provided in WO2007092372.

It is observed that the rate of conversion of Regadenoson monohydrate (Form A) to Regadenoson Form C is dependent on the solvent and/or reaction temperature.

When isopropanol is used as the reaction solvent, it is observed that complete conversion of Form A to Form C does not occur even after 7 hours, if the reaction temperature is less than about 60° C. However, when the reaction temperature is about 70° C. or above about 70° C., complete conversion of Form A to Form C occurs in about 3 to 7 hours.

According to one embodiment of the present invention, there is provided a process for preparation of Regadenoson Form C, comprising the steps of,
a) treating Regadenoson with a $C_1$-$C_3$ alcohol at an elevated temperature to obtain a mixture;
b) maintaining said mixture at the same temperature for at least about 3 hours; and
c) isolating Regadenoson Form C from said mixture.

Preferably, the elevated temperature is a temperature above 70° C.

Preferably, the $C_1$-$C_3$ alcohol is selected from isopropanol, n-propanol or ethanol. Preferably, the mixture is maintained at an elevated temperature for at least about 5 hours, more preferably for at least about 7 hours.

Preferably, the isolation of Regadenoson Form C is carried out by cooling the mixture to about 70° C.

In a preferred embodiment, Regadenoson monohydrate (Form A) is treated with isopropanol to obtain a mixture (suspension). The obtained suspension is heated to reflux and maintained under stirring at the same temperature for at least about 3 hours, preferably for at least about 5 hours, more preferably for at least about 7 hours. The hot mixture is then cooled to about 60° C. to 80° C., preferably about 65° C. to 75° C., more preferably about 70° C. and then filtered to isolate Regadenoson Form C.

In another preferred embodiment, Regadenoson monohydrate (Form A) is treated with isopropanol to obtain a mixture (suspension). The obtained suspension is heated to reflux and maintained under stirring at the same temperature for about 7-8 hours. The hot mixture is then cooled to about 60° C. to 80° C., preferably about 65° C. to 75° C., more preferably, about 70° C. and then filtered to isolate Regadenoson Form C.

In another preferred embodiment. Regadenoson monohydrate (Form A) is treated with isopropanol to obtain a mixture (suspension). The obtained suspension is heated to reflux and maintained under stirring at the same temperature for about 6 hours. The hot mixture is then cooled to about 60° C. to 80° C., preferably about 65° C. to 75° C., more preferably about 70° C. and then filtered to isolate Regadenoson Form C.

In another preferred embodiment, Regadenoson monohydrate (Form A) is treated with isopropanol to obtain a mixture (suspension). The obtained suspension is heated to reflux and maintained under stirring at the same temperature for about 12 hours. The hot mixture is then cooled to about 60° C. to 80° C., preferably about 65° C. to 75° C., more preferably about 70° C. and then filtered to isolate Regadenoson Form C.

In another preferred embodiment, Regadenoson monohydrate (Form A) is treated with isopropanol to obtain a mixture (suspension). The obtained suspension is heated to reflux and maintained under stirring at the same temperature for about 24 hours. The hot mixture is then cooled to about 60° C. to 80° C., preferably about 65° C. to 75° C., more preferably about 70° C. and then filtered to isolate Regadenoson Form C.

Ethanol or n-propanol can be used in place of isopropanol, for the preparation of Regadenoson Form C.

Regadenoson Form C obtained by the process of the present invention can be isolated by techniques such as filtration, distillation, centrifugation or slow evaporation. Preferably, Regadenoson Form C is isolated by filtration. The isolated crystals are then washed with a suitable solvent and then dried at a temperature of about 50 to 70° C. Drying of the crystals may be carried out by techniques known in the art. Preferably, the drying of Regadenoson Form C crystals is carried out using air tray dryer or vacuum tray dryer. The drying may be carried out for sufficient periods to obtain the product with the desired quality.

Regadenoson Form C obtained by the process of the present invention has a moisture content in the range of 0.5 to 4.4% w/w. However, this variation in the moisture content does not have any effect on the XRPD pattern of Regadenoson Form C.

Figure 1B:
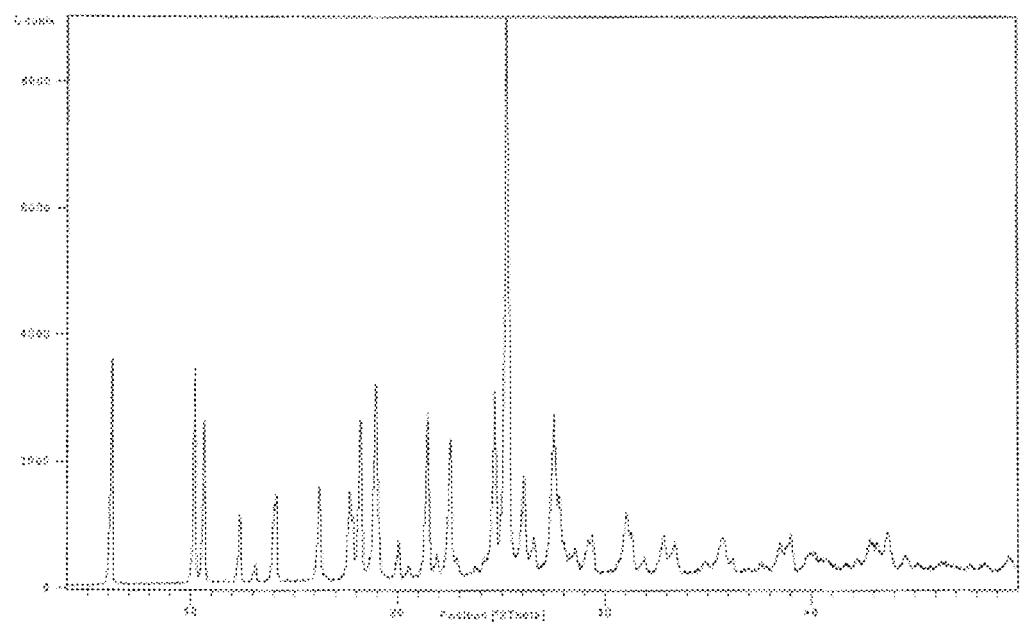
FIG. 1B: XRPD of Regadenoson Form C obtained by the process of the present invention.

Regadenoson Form C obtained by the process of the present invention is characterized by X-ray powder diffraction pattern as shown in FIG. 1A or 1B. It is further characterized by peaks expressed as 2-theta values at about 6.16, 10.36, 10.72, 12.32 and 25.41 degrees.

Regadenoson Form C obtained by the process of the present invention is found to be stable.

Figure 2:
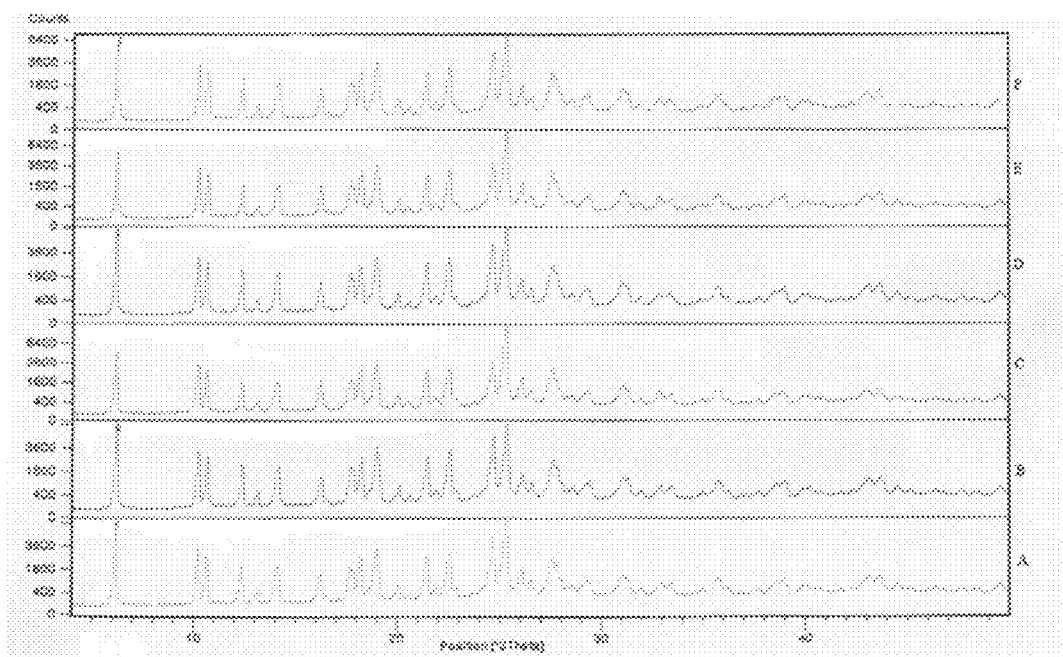
FIG. 2: XRPD of Regadenoson Form C samples, stored for one month at different stability testing conditions.

XRPD patterns of Regadenoson Form C samples, stored for one month, at different stability testing conditions are shown in FIG. 2.

The explanation of the labels used in FIG. 2 is as provided below,
A: XRPD of Form C sample stored for one month, at 40° C. and 75% RH
B: XRPD of Form C sample stored for one month, at 30° C. and 65% RH
C: XRPD of Form C sample stored for one month, at 25° C. and 60% RH
D: XRPD of Form C sample stored for one month, at 20° C. and 45% RH
E: XRPD of Form C sample stored for one month at 2-8° C.
F: XRPD of Form C (Initial)

Figure 3:
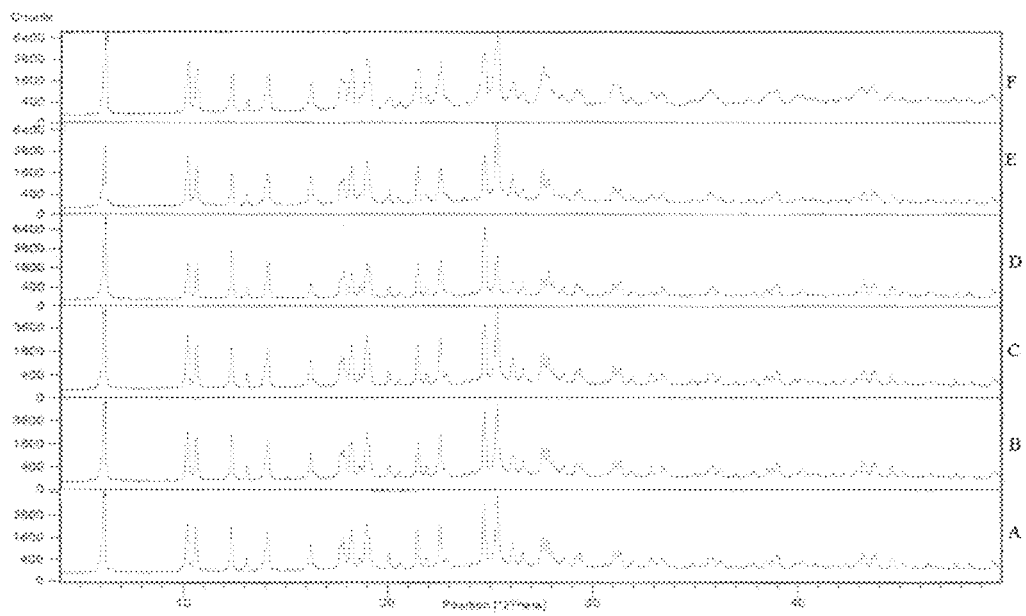
FIG. 3: XRPD of Regadenoson Form C samples, stored for three months at different stability testing conditions.

XRPD patterns of Regadenoson Form C samples, stored for three months, at different stability testing conditions are as shown in FIG. 3.

The explanation of the labels used in FIG. 3 is as provided below,
A: XRPD of Form C sample stored for three months, at 40° C. and 75% RH
B: XRPD of Form C sample stored for three months, at 30° C. and 65% RH
C: XRPD of Form C sample stored for three months, at 25° C. and 60% RH
D: XRPD of Form C sample stored for three months, at 20° C. and 45% RH
E: XRPD of Form C sample stored for three months, at 2-8° C.
F: XRPD of Form C (Initial)

Figure 4:
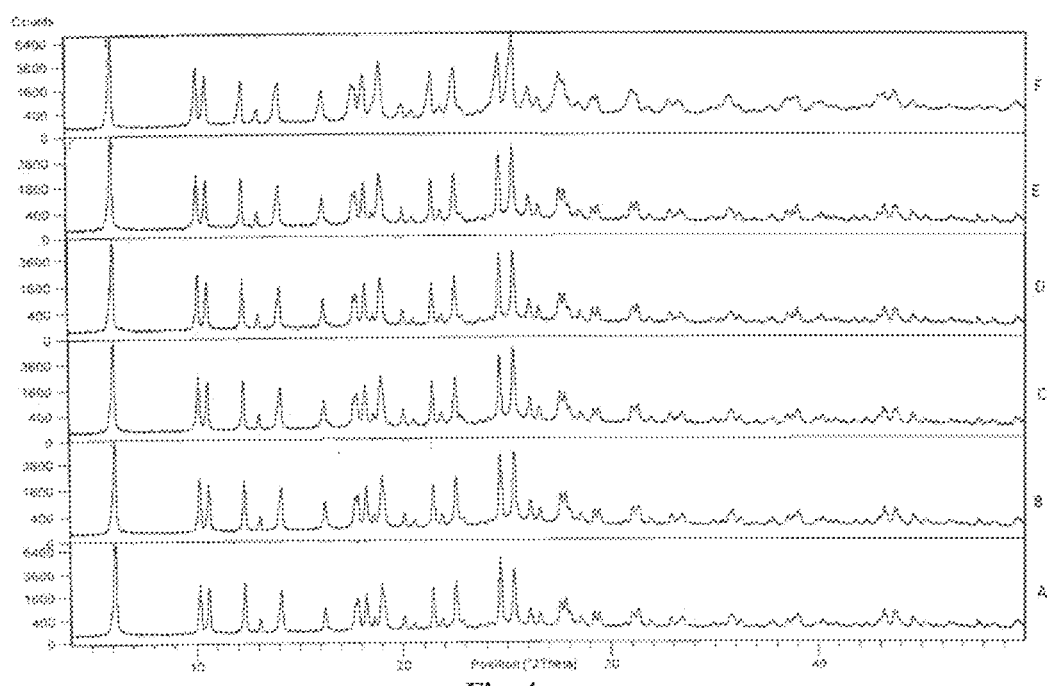
FIG. 4: XRPD of Regadenoson Form C samples, stored for six months at different stability testing conditions.

XRPD patterns of Regadenoson Form C samples, stored for six months, at different stability testing conditions are as shown in FIG. 4.

The explanation of the labels used in FIG. 4 is as provided below,
A: XRPD of Form C sample stored for six months, at 40° C. and 75% RH
B: XRPD of Form C sample stored for six months, at 30° C. and 65% RH
C: XRPD of Form C sample stored for six months, at 25° C. and 60% RH
D: XRPD of Form C sample stored for six months, at 20° C. and 45% RH
E: XRPD of Form C sample stored for six months, at 2-8° C.
F: XRPD of Form C (Initial)

Figure 5:
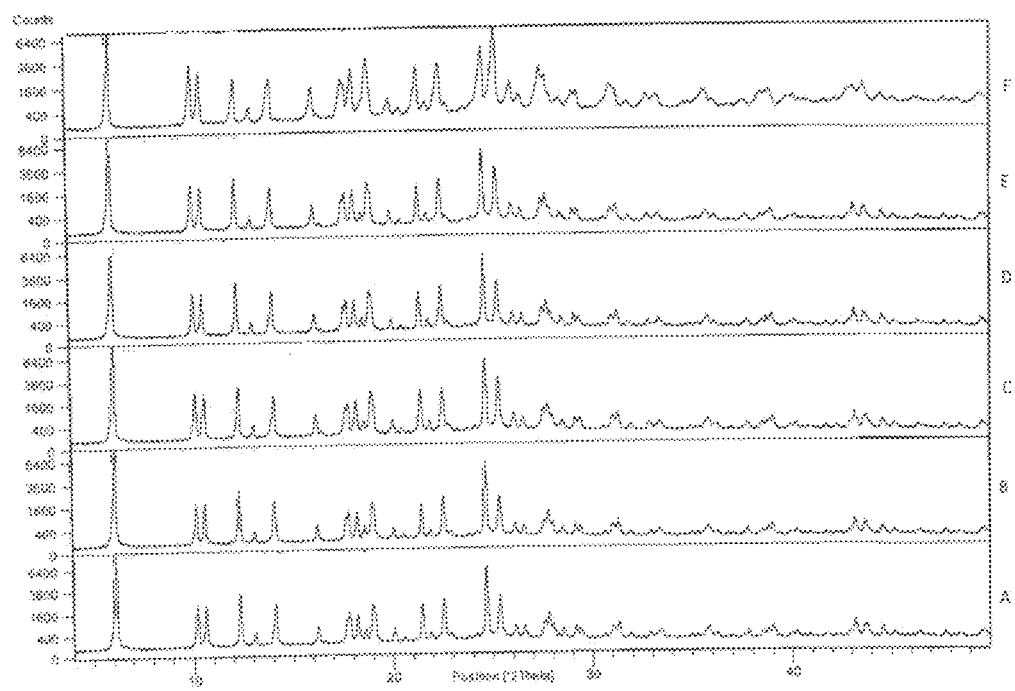
FIG. 5: XRPD of Regadenoson Form C samples, stored for nine months at different stability testing conditions.

XRPD patterns of Regadenoson Form C samples, stored for nine months, at different stability testing conditions are as shown in FIG. 5.

The explanation of the labels used in FIG. 5 is as provided below,
A: XRPD of Form C sample stored for nine months, at 40° C. and 75% RH
B: XRPD of Form C sample stored for nine months, at 30° C. and 65% RH
C: XRPD of Form C sample stored for nine months, at 25° C. and 60% RH
D: XRPD of Form C sample stored for nine months, at 20° C. and 45% RH
E: XRPD of Form C sample stored for nine months, at 2-8° C.
F: XRPD of Form C (Initial)

Figure 6:
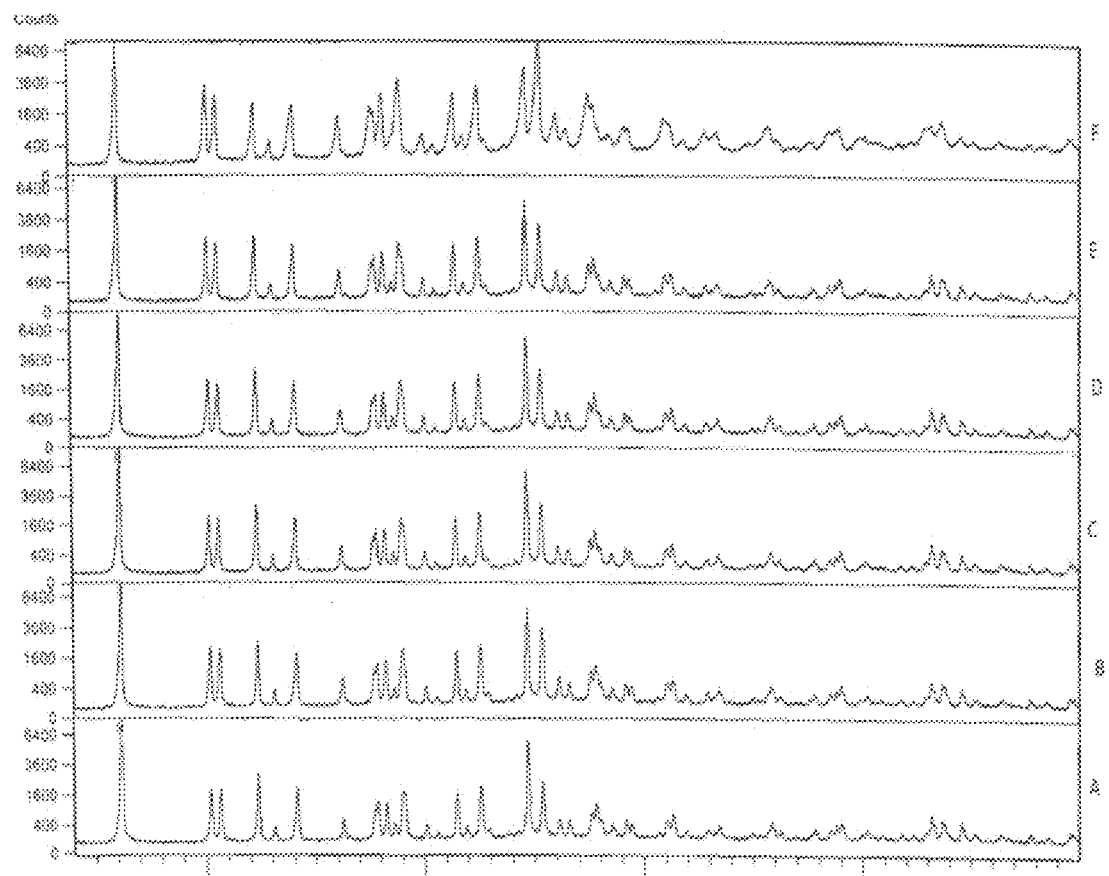
FIG. 6: XRPD of Regadenoson Form C samples, stored for twelve months at different stability testing conditions.

XRPD patterns of Regadenoson Form C samples, stored for twelve months, at different stability testing conditions are as shown in FIG. 6.

The explanation of the labels used in FIG. 6 is as provided below.
A: XRPD of Form C sample stored for twelve months, at 40° C. and 75% RH
B: XRPD of Form C sample stored for twelve months, at 30° C. and 65% RH
C: XRPD of Form C sample stored for twelve months, at 25° C. and 60% RH
D: XRPD of Form C sample stored for twelve months, at 20° C. and 45% RH
E: XRPD of Form C sample stored for twelve months, at 2-8° C.
F: XRPD of Form C (Initial)

Regadenoson Form C obtained by the process of the present invention was found to be stable, when subjected to various stability testing conditions.

Another embodiment of the present invention provides substantially pure Regadenoson Form C. Regadenoson Form C obtained by the process of the present invention has purity greater than 99%, preferably greater than 99.5%, more preferably greater than 99.8%.

Regadenoson monohydrate (Form A) used in the process of the present invention can be prepared by any known method or as described in our pending Indian Patent Application, 3310/MUM/2012.

In a preferred embodiment, to an aqueous solution of methylamine is added Ethyl 1-{9-[(4S,2R,3R,5R)-3,4-dihydroxy-5-(hydroxymethyl)oxolan-2-yl]-6-aminopurin-2-yl}pyrazol-4-carboxylate at a temperature of about 0-5° C.

to obtain a mixture. The reaction mixture is stirred at the same temperature for about 3 to 8 hours, preferably for 5 hours to obtain a slurry. The temperature of the slurry is allowed to reach to about 15 to 25° C., preferably 18 to 20° C. The slurry is maintained under stirring at the same temperature for about 2 to 6 hours, preferably for 3 hours. The slurry is then treated with water to obtain a mixture. This mixture is stirred for about 30 to 90 minutes, preferably for 60 minutes at the same temperature followed by filtration to obtain a solid. The solid thus obtained is washed with water and/or suitable solvent and then dried to obtain Regadenoson as an off-white to pale brown coloured solid. The obtained Regadenoson is further purified.

In a preferred embodiment, the process for purification of Regadenoson comprises, suspending Regadenoson in a first solvent selected from DMF, acetonitrile, dichloromethane, ethyl acetate, acetone, tetrahydrofuran or DMSO to obtain a mixture. The mixture is warmed to a temperature of about 30 to 50° C., preferably 35 to 40° C. and stirred for 10 to 30 min, preferably for 15 to 20 min to obtain a brown solution. The obtained brown solution is filtered to remove any undissolved/suspended particles. The filtrate obtained is treated with a second solvent selected from isopropanol, methanol, ethanol, n-propanol or butanol, over a period of 5-10 min to obtain a mixture. The mixture is stirred for 2 to 6 hours, preferably for 3 to 4 hours to obtain a slurry. The slurry is filtered to obtain a solid. The solid is washed with the second solvent and then suspended in water to obtain a slurry. The resultant slurry is maintained for about 1 hour at 25 to 30° C. followed by filtration to obtain a solid. The solid is washed with water and/or second solvent followed by drying to obtain an off-white coloured solid having purity of more than 99.5%.

In another preferred embodiment, the process for purification of Regadenoson comprises, suspending Regadenoson in a solvent selected from methanol, ethanol, n-propanol or isopropanol to obtain a suspension. The suspension is maintained under stirring for 1 to 4 hours, preferably for 3 hours at a temperature of about 20 to 40° C., preferably 25 to 30° C. The mixture thus obtained is treated with water to obtain a slurry. The slurry is filtered to obtain a solid which is washed with water and/or an alcoholic solvent followed by drying to obtain a white coloured solid having purity of more than 99.5%.

Another embodiment of the present invention provides a pharmaceutical composition comprising Regadenoson, in particular Regadenoson Form C prepared by the process of the present invention.

Preferably, Regadenoson Form C is treated with excipient (s) selected from the group consisting of disodium edetate, dibasic sodium phosphate dihydrate, dibasic sodium phosphate anhydrous, monobasic sodium phosphate monohydrate and propylene glycol to obtain a pharmaceutical composition.

Another embodiment of the present invention provides a process for preparation of a pharmaceutical composition of Regadenoson Form C comprising the steps of:
a) dissolving disodium edetate, dibasic sodium phosphate dihydrate, monobasic sodium phosphate monohydrate and propylene glycol in water to obtain Solution I;
b) dissolving Regadenoson Form C in Solution I to obtain Solution II;
c) checking the pH of Solution II and then making up the volume of Solution II upto q.s. with water;
d) filtering Solution II through 0.45μ filter and 0.22μ sterile filter; and
e) filling the desired volume into PFS or vials.

Preferably, the dissolution is carried out at room temperature or at a higher temperature.

The pH of the composition is between 6.3 and 7.7.

Unless otherwise indicated, the following definitions are set forth to illustrate and define the meaning and scope of the various terms used to describe the invention herein.

The term "reflux" or "reflux temperature" means the temperature at which the solvent or solvent system refluxes or boils at atmospheric pressure.

The term "elevated temperature" means any temperature above 40° C., preferably above 60° C., more preferably above 70° C.

The term "substantially pure" means Regadenoson or Regadenoson Form C having less than about 1%, preferably less than about 0.5%, more preferably less than about 0.3%, most preferably less than about 0.15% of undesired compounds including other polymorphic forms.

X-ray powder diffraction pattern was obtained on PANalytical Xpert'PRO diffractometer equipped with accelerator detector using Copper K$\alpha$ (n=1.5406 A°) radiation with scanning range between 2-theta 4-50 at a scanning speed of 0.042849°/sec.

The following examples are for illustrative purposes only and are not intended to limit the scope of the invention in any way.

EXAMPLES

Example 1: Preparation of Regadenoson Form a (Monohydrate)

40% aqueous solution of methylamine (1500 ml, 17.37 mol) was charged in a flask and cooled to 0-5° C. To this cooled solution, Pyrazoloadenosine (50 g, 0.123 mol) was added to obtain a mixture. The mixture was stirred at the same temperature for 5 hours to obtain a slurry. The temperature of the slurry was allowed to reach to 18-20° C. and the slurry was maintained under stirring at the same temperature for 3 hours. Water (500 ml) was added to the slurry to obtain a mixture. The mixture was stirred for 1 hour at 18-20° C. and filtered to obtain a solid. The obtained solid was washed with water (3×100 ml), IPA (3×100 ml) and dried at 25-30° C. to obtain off-white to pale brown coloured solid.

Yield: 40 g (80%); Purity: more than 98%

Example 2A: Purification of Regadenoson Form a (Monohydrate)

Regadenoson (10 g) was suspended in DMF (100 ml) to obtain a suspension. The suspension was warmed to 35-40° C. and stirred for 15-20 min to obtain a brown solution. The brown solution was filtered to remove undissolved/suspended particles. The filtrate obtained was added in IPA (300 ml) over a period of 5-10 min to obtain a mixture. The mixture was stirred for 3-4 hours to obtain a slurry. The slurry was filtered to obtain a solid. The solid was washed with IPA (3×40 ml) and was suspended in water (100 ml). The resultant slurry was maintained for 1 hour at 25-30° C. followed by filtration to obtain a solid. The solid was washed with water (20 ml) followed by IPA (2×20 ml) and dried at 25-30° C. to obtain off-white coloured solid.

Yield: 6.5 g (65%): Purity: more than 99.8%

Example 2B: Purification of Regadenoson Form a (Monohydrate)

Regadenoson (10 g) was suspended in methanol (100 ml) to obtain a suspension. The suspension was stirred for 3 hours at 25-30° C. and then treated with water (100 ml) to obtain a mixture. This mixture was stirred for 1-2 hours and then filtered to obtain a solid. The solid was washed with water (2×20 ml) followed by IPA (2×20 ml) and then dried at 40-50° C. to obtain a white coloured solid.

Yield: 9 g (90%); Purity: more than 99.8%

Example 3: Preparation of Regadenoson Form C

Regadenoson monohydrate (5 g) was suspended in isopropanol (75 ml) to obtain a suspension. The obtained suspension was heated to reflux and maintained under stirring at the same temperature for about 7-8 hours. The obtained mixture was then cooled to about 70° C. and then filtered to isolate Regadenoson Form C, which was dried at 65° C.

Yield: 4.5 g (90%); Purity: more than 99.8%

Example 4: Preparation of Regadenoson Form C

Regadenoson monohydrate (93 g) was suspended in isopropanol (1395 ml) to obtain a suspension. The obtained suspension was heated to reflux and maintained under stirring at the same temperature for about 24 hours. The obtained mixture was then cooled to about 75° C. and then filtered to isolate Regadenoson Form C, which was dried at 65° C.

Yield: 84.5 g (90.86%); Purity: more than 99.97%
$K_f$=1.41% w/w

Example 5: Preparation of Regadenoson Form C

Regadenoson monohydrate (52 g) was suspended in isopropanol (780 ml) to obtain a suspension. The obtained suspension was heated to reflux and maintained under stirring at the same temperature for about 6 hours. The obtained mixture was cooled to about 75° C. and then filtered to isolate Regadenoson Form C, which was dried at 65° C.

Yield: 46.9 g (90.0%); $K_f$=2.35% w/w

The dried sample (46 gm) was again suspended in isopropanol (920 ml) to obtain a suspension. The obtained suspension was heated to reflux and maintained under stirring at the same temperature for about 6 hours. The obtained mixture was then cooled to about 75° C. and then filtered to isolate Regadenoson Form C, which was dried at 65° C.

Yield: 44.5 g (96.0%): $K_f$=2.2% w/w

Example 6: Preparation of Regadenoson Form C

Regadenoson monohydrate (45 g) was suspended in isopropanol (675 ml) to obtain a suspension. The obtained suspension was heated to reflux and maintained under stirring at the same temperature for about 24 hours. The obtained mixture was then cooled to about 75° C. and then filtered to isolate Regadenoson Form C, which was dried at 65° C.

Yield: 42.1 g (93.5%); Purity: more than 99.9%
$K_f$=0.99% w/w

Example 7: Preparation of Regadenoson Form C

Regadenoson monohydrate (45 g) was suspended in isopropanol (675 ml) to obtain a suspension. The obtained suspension was heated to reflux and maintained under stirring at the same temperature for about 24 hours. The obtained mixture was then cooled to about 75° C. and then filtered to isolate Regadenoson Form C, which was dried at 65° C.

Yield: 43 g (95.5%); Purity: more than 99.9%
$K_f$=1.22% w/w

We claim:

1. A process for preparation of Regadenoson Form C comprising the steps of,
    a) treating Regadenoson with a $C_1$-$C_3$ alcohol selected from isopropanol, n-propanol or ethanol at an elevated temperature to obtain a mixture;
    b) maintaining said mixture at the same temperature for at least about 3 hours; and
    c) isolating Regadenoson Form C from said mixture by cooling said mixture to about 70° C.

2. The process as claimed in claim 1, wherein said elevated temperature is a temperature above 70° C.

3. The process as claimed in claim 1, wherein said mixture is maintained at an elevated temperature for at least about 7 hours.

4. The process as claimed in claim 1, wherein said Regadenoson is Regadenoson monohydrate.

5. The process as claimed in claim 1, wherein said Regadenoson Form C has a moisture content in the range of 0.5-4.4% w/w.

6. The process as claimed in claim 1, wherein said Regadenoson Form C is characterized by a X-ray diffraction pattern having peaks at 2-theta values of about 6.16, 10.36, 10.72, 12.32 and 25.41 degrees.

7. The process as claimed in claim 1, wherein said Regadenoson Form C is further treated with one or more excipient(s) selected from the group consisting of disodium edetate, dibasic sodium phosphate dihydrate, dibasic sodium phosphate anhydrous, monobasic sodium phosphate monohydrate and propylene glycol to obtain a pharmaceutical composition.

* * * * *